United States Patent [19]

Berndt et al.

[11] Patent Number: 5,659,018

[45] Date of Patent: Aug. 19, 1997

[54] MOCARHAGIN, A COBRA VENOM PROTEASE, AND THERAPEUTIC USES THEREOF

[75] Inventors: Michael C. Berndt, Mt Eliza; Lindsay Dunlop, Kirwan; Robert Andrews, Hampton; Mariagrazia DeLuca, Dandenong North, all of Australia

[73] Assignee: Genetics Institute, Inc., Cambridge, Mass.

[21] Appl. No.: 520,977

[22] Filed: Aug. 1, 1995

[51] Int. Cl.$^6$ .............................. C07K 1/00; C07K 14/00; C07K 17/00; A23J 1/00

[52] U.S. Cl. .................... 530/400; 530/350; 530/412; 530/413; 530/417; 435/183

[58] Field of Search ........................................ 530/350, 400, 530/412, 413, 417; 435/183

[56] References Cited

PUBLICATIONS

Paine et al., J. Biol. Chem. 267:22869–22876 (1992).
Takeya et al., J. Biochem. (Tokyo) 106:151–157 (1989).
Takeya et al., J. Biol. Chem. 265:16068–16073 (1993).
Neeper et al., Nucleic Acids Res. 18:4255 (1990).
Ogilvie & Gartner, J. Herpetology 18(3), 285–290 (1984).
Gartner and Ogilvie. Biochem. J. 224:301–307 (1984).
Au et al., Biochem & Biophys Res. Comm. 181(2):585–593 (1991).

*Primary Examiner*—Christina Y. Chan
*Assistant Examiner*—Patrick J. Nolan
*Attorney, Agent, or Firm*—Scott A. Brown; Thomas J. DeRosier

[57] ABSTRACT

Mocarhagin, a cobra venom protease, is disclosed. Pharmaceutical compositions and therapeutic uses of the protease are also provided.

2 Claims, 6 Drawing Sheets

FIG. 1.

```
                          PACE          Mocarhagin
                                    ↓      ↓
PSGL-1:   R D R R  Q A T E Ⓨ E Ⓨ L D Ⓨ D F L P E T E P P E M L
                   1                10                      20

GP Ibα:   D E G D T D L Ⓨ D Ⓨ Ⓨ P E E D T E G D
          273                              291
                                   ↑
                               Mocarhagin
```

| | | | | | | | | | | | | | | | | | | | | | |
|---|---|---|---|---|---|---|---|---|---|---|---|---|---|---|---|---|---|---|---|---|---|
| Mocarhagin: | T | K/N | C | P | E | L | I/K | P | Y | L | Q | K/A | C | Y | I | E | F | Y | V | V | V | D | N |
| Jararhagin: | | | | | E | Q | Q | R | Y | - | D | P | Y | K | Y | I | E | F | F | V | V | V | D | Q |
| HB1B: | | | | | E | Q | - | R | E | - | - | P | R | R | Y | I | K | L | A | I | V | V | D | H |
| Pro-Trig: | | | | | E | Q | Q | R | F | - | - | P | Q | R | Y | I | K | L | G | I | F | V | D | H |
| Pro-Rhod: | | | | | E | - | - | - | - | - | - | I | K | R | H | V | D | I | V | - | V | V | D | S |
| HR2A: | | | | | E | Q | - | R | F | - | - | P | Q | R | T | I | E | L | A | I | V | V | D | H |

FIG. 6

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( x i ) SEQUENCE DESCRIPTION: SEQ ID NO:1:

```
Thr  Xaa  Cys  Pro  Glu  Leu  Xaa  Pro  Tyr  Leu  Gln  Xaa  Lys  Cys  Tyr  Ile
 1              5                        10                       15
Glu  Phe  Tyr  Val  Val  Val  Asp  Asn
              20
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
Gln  Ala  Thr  Glu  Tyr  Glu  Tyr  Leu  Asp  Tyr  Asp  Phe  Leu  Pro  Glu
 1              5                        10                       15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

```
Thr  Glu  Tyr  Glu  Tyr  Leu  Asp  Tyr  Asp  Phe  Leu  Pro  Glu  Thr  Glu
 1              5                        10                       15
```

( 2 ) INFORMATION FOR SEQ ID NO:4:

( i ) SEQUENCE CHARACTERISTICS:

(A) LENGTH: 15 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

```
Asp Tyr Asp Phe Leu Pro Glu Thr Glu Pro Pro Glu Met Leu Arg
1               5                   10                  15
```

(2) INFORMATION FOR SEQ ID NO:5:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

```
Gln Ala Thr Glu Tyr Glu Tyr Leu Asp Tyr
1               5                   10
```

(2) INFORMATION FOR SEQ ID NO:6:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO:6:

```
Asp Phe Leu Pro Glu Thr Glu Pro Pro Glu Met Leu
1               5                   10
```

(2) INFORMATION FOR SEQ ID NO:7:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:7:

```
Arg Asp Arg Arg Gln Ala Thr Glu Tyr Glu Tyr Leu Asp Tyr Asp Phe
1               5                   10                  15
Leu Pro Glu Thr Glu Pro Pro Glu Met Leu
                20                  25
```

(2) INFORMATION FOR SEQ ID NO:8:

(i) SEQUENCE CHARACTERISTICS:
(A) LENGTH: 19 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:8:

```
Asp Glu Gly Asp Thr Asp Leu Tyr Asp Tyr Tyr Pro Glu Glu Asp Thr
1               5                   10                  15
```

Glu Gly Asp ( 2 ) INFORMATION FOR SEQ ID NO:9:

( i ) SEQUENCE CHARACTERISTICS:
    ( A ) LENGTH: 19 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:9:

```
Glu Gln Gln Arg Tyr Asp Pro Tyr Lys Tyr Ile Glu Phe Phe Val Val
 1               5                  10                  15
Val Asp Gln
```

( 2 ) INFORMATION FOR SEQ ID NO:10:

( i ) SEQUENCE CHARACTERISTICS:
    ( A ) LENGTH: 17 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:10:

```
Glu Gln Arg Glu Pro Arg Arg Tyr Ile Lys Leu Ala Ile Val Val Asp
 1               5                  10                  15
His
```

( 2 ) INFORMATION FOR SEQ ID NO:11:

( i ) SEQUENCE CHARACTERISTICS:
    ( A ) LENGTH: 17 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:11:

```
Glu Gln Arg Phe Pro Gln Arg Thr Ile Glu Leu Ala Ile Val Val Asp
 1               5                  10                  15
His
```

( 2 ) INFORMATION FOR SEQ ID NO:12:

( i ) SEQUENCE CHARACTERISTICS:
    ( A ) LENGTH: 18 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:12:

```
Glu Gln Gln Arg Phe Pro Gln Arg Tyr Ile Lys Leu Gly Ile Phe Val
 1               5                  10                  15
Asp His
```

( 2 ) INFORMATION FOR SEQ ID NO:13:

( i ) SEQUENCE CHARACTERISTICS:
    ( A ) LENGTH: 14 amino acids ( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:13:

```
Glu  Ile  Lys  Arg  His  Val  Asp  Ile  Val  Val  Val  Val  Asp  Ser
 1              5                        10
```

MOCARHAGIN, A COBRA VENOM PROTEASE, AND THERAPEUTIC USES THEREOF

BACKGROUND OF THE INVENTION

In response to inflammatory stimuli, neutrophils in the adjacent vasculature initially roll on the blood vessel wall, then stick, and finally transmigrate to the site of insult. The initial rolling event involves a class of adhesion proteins termed selectins (P-, E-, and L-selectin) which mediate the interaction between leukocytes and endothelial cells by their recognition of specific carbohydrate counter-structures, including sialyl-Lewis x. The primary sequence/motif structure of each of the selectins is similar. Each contains a N-terminal, 118-amino acid calcium-dependent lectin domain, an EGF motif, a variable number of tandem repetitive motifs related to motifs found in complement regulatory domains, a transmembrane domain and a short cytoplasmic tail.

P-selectin is a 140-kDa integral granule membrane glycoprotein localized to platelet-granules and the Weibel-Palade bodies of endothelial cells and is rapidly expressed on both cell types on cell activation. This suggests that endothelial P-selectin is a critical molecule mediating initial adhesion events in acute inflammation, a view recently supported by a number of in vivo inflammatory models including neutrophil-dependent acute lung injury (Mulligan et al. (1992) J. Clin. Invest. 90, 1600), endotoxin-induced neutropenia (Coughlan et al. (1994) J. Exp. Med. 179, 329), reperfusion injury (Asako et al. (1994) J. Clin. Invest. 93, 1508) and histamine-induced leukocyte rolling in post capillary venules (Weyrich et al. (1993) J. Clin. Invest. 91, 2620). P-selectin binds to 10,000–20,000 copies of a single class of binding sites on neutrophils and HL60 cells.

Sako et al. ((1993) Cell 75, 1179) have cloned the ligand for P-selectin, termed P-selectin glycoprotein ligand-1 (PSGL-1) (see also copending application Ser. No. 08/316, 305). PSGL-1 is a 220 kDa, disulfide-linked homodimeric sialomucin which, when expressed in COS cells with the appropriate fucosyltransferase, binds P-selectin in a similar calcium-dependent manner to the receptor on neutrophis. PSGL-1 has a signal peptide sequence of 17 amino acids followed by a 24-amino acid PACE propeptide sequence. The mature N-terminus of PSGL-1 contains an unusual stretch of twenty amino acids which is rich in negatively-charged aspartate and glutamate residues and which contains three tyrosine residues which meet the consensus sequence for 0-sulfation by a golgi sulfotransferase. At least one of these tyrosine residues is sulfated as evaluated by site-directed mutagenesis.

In addition to binding P-selectin, PSGL-1 also binds E-selectin. In contrast to P-selectin, however, the requirements for E-selectin recognition are much less rigid. E-selectin binds a wide variety of sialomucin structures if they co-express the sialyl-Lewis x structure. L-selectin binds to a number of different counter-receptors, GLYCAM-1, MadCAM-1 and CD34, which like PSGL-1, are also sialomucins. A major question currently unresolved is what determines selectin specificity in the recognition of specific counter-receptor structures. P-, E- and L-selectin are 60–70% homologous in their N-terminal, 118-amino acid lectin motifs and each similarly recognizes the sialyl-Lewis x and sialyl-Lewis a carbohydrate structures. Further, binding of P-selectin to its receptor on neutrophils is four to five orders of magnitude more avid than the binding of sialyl-Lewis x. While differences in specificity and avidity may in part be accounted for by either the presentation of multiple sialyl-Lewis carbohydrate structure, it is probable that the protein component of the sialomucin also determines selectin interaction.

Although the inflammatory response mediated by the P-selectin/PSGL-1 interaction is a part of the body's normal defense system, over aggressive inflammatory responses can also result in the development of various inflammatory disease states. It would, therefore, be desirable to provide agents for interfering with or blocking the P-selectin/PSGL-1 interaction in order to treat inflammatory disease.

SUMMARY OF THE INVENTION

The present invention provides compositions comprising a mocarhagin protein substantially free of other cobra proteins. In preferred embodiments, the mocarhagin protein is full-length mocarhagin (as described below). In other embodiments, the mocarhagin protein is a fragment of full-length mocarhagin having mocarhagin proteolytic activity. Preferably, the mocarhagin protein is characterized by at least one characteristic selected from the group consisting of:

(a) a molecular weight of approximately 55 kDa under reducing conditions;

(b) a molecular weight of approximately 55 kDa under nonreducing conditions;

(c) an N-terminal amino acid sequence comprising Thr-Xaa-Cys-Pro-Glu-Leu-Xaa-Pro-Tyr-Leu-Gln-Xaa-Lys-Cys-Tyr-Ile-Glu-Phe-Tyr-Val-Val-Val-Asp-Asn (SEQ ID NO:1), wherein the Xaa in the second position is Lys or Asn, the Xaa in the seventh position is Ile or Lys, and the Xaa in the twelfth position is Lys or Ala;

(d) mocarhagin proteolytic activity;

(e) the ability to inhibit platelet binding to vWF;

(f) requirement of calcium ion for activity;

(g) requirement of zinc ion for activity;

(h) an activity substantially inhibited by excess EDTA; and (i) an activity substantially inhibited by high concentrations of DFP.

In particularly preferred embodiments, the mocarhagin protein is capable of cleaving PSGL-1. Compositions comprising a therapeutically effective amount of a mocarhagin protein and a pharmaceutically acceptable carrier are also provided.

Methods of treating an inflammatory disease and of inhibiting selectin-mediated binding comprising administering a therapeutically effective amount of a pharmaceutical composition comprising a mocarhagin protein to a mammalian subject are disclosed.

The invention also provides a method of isolating mocarhagin from venom, said method comprising:

(a) subjecting a composition comprising cobra venom to a heparin affinity chromatography column; and (b) eluting mocarhagin from said heparin affinity column. Other methods of purification of mocarhagin encompassed by the present invention further comprise:

(c) subjecting the eluate from said heparin affinity column to a gel filtration column; and (d) eluting mocarhagin from said gel filtration column. Compositions comprising a protein isolated according to these methods (and optionally further comprising a pharmaceutically acceptable carrier) are also encompassed by the claimed invention. Such compositions can also be used in methods of treating an inflammatory disease and of inhibiting selectin-mediated binding which comprise administering a therapeutically effective amount of such compositions to a mammalian subject.

Compositions comprising an antibody which specifically reacts with the mocarhagin or a fragment thereof having mocarhagin proteolytic activity are also provided.

BRIEF DESCRIPTION OF THE FIGURES

FIG. 6: Comparison of the N-terminal amino acid sequence determined for mocarhagin (SEQ. ID NO:1) with metalloprotease-disintegrins from viper venom. Jararhagin (SEQ. ID NO:9) is a 52-kDa protease purified from *Bothrops jararaca* (Paine et al. (1992) J. Biol. Chem. 267, 22869–22876), HR1B (SEQ. ID NO:10) and Hr2A (SEQ. ID NO:11) are hemorrhagins derived from *Trimeresurus flavoviridis* (Habu) venom (Takeya et al. (1989) J. Biochem. (Tokyo) 106, 151–157; Takeya et al. (1990) J. Biol. Chem. 265, 16068–16073); the sequences for protrigramin (SEQ. ID NO:12) and pro-rhodostomin (SEQ. ID NO:13) are inferred from the cDNA sequences of the disintegrins trigramin (from *T. gramineus* venom (Neeper et al. (1990) Nucleic Acids Res. 18, 4255)) and rhodostomin (from *Calloselasma rhodostoma* (Malayan pit viper) venom (Au et al. (1991) Biochem. Biophys. Res. Commun. 181, 585–593)). Identical or conserved residues are boxed.

DETAILED DESCRIPTION OF THE INVENTION AND PREFERRED EMBODIMENTS

The present invention provides a highly specific metalloproteinase, mocarhagin, which has been purified from the venom of the Mozambiquan spitting cobra, *Naja mocambique mocambique*. Mocarhagin cleaves a ten amino acid peptide from the mature N-terminus of PSGL-1 and abolishes the ability of PSGL-1 to bind P-selectin. These results are in accord with the negative charge/sulfated tyrosine cluster at the N-terminus of PSGL-1 being an important determinant of P-selectin recognition in addition to the recognition of carbohydrate structure.

Mocarhagin can be purified from cobra venom according to the method described in the examples below. Other methods of purifying mocarhagin from cobra venom will also be apparent to those skilled in the art. The progress of any purification scheme for mocarhagin can be monitored on the basis of the biochemical characteristics of mocarhagin described herein and the assays for PSGL-1 digestion and neutrophil/HL60 cell binding described below.

Figure 5:
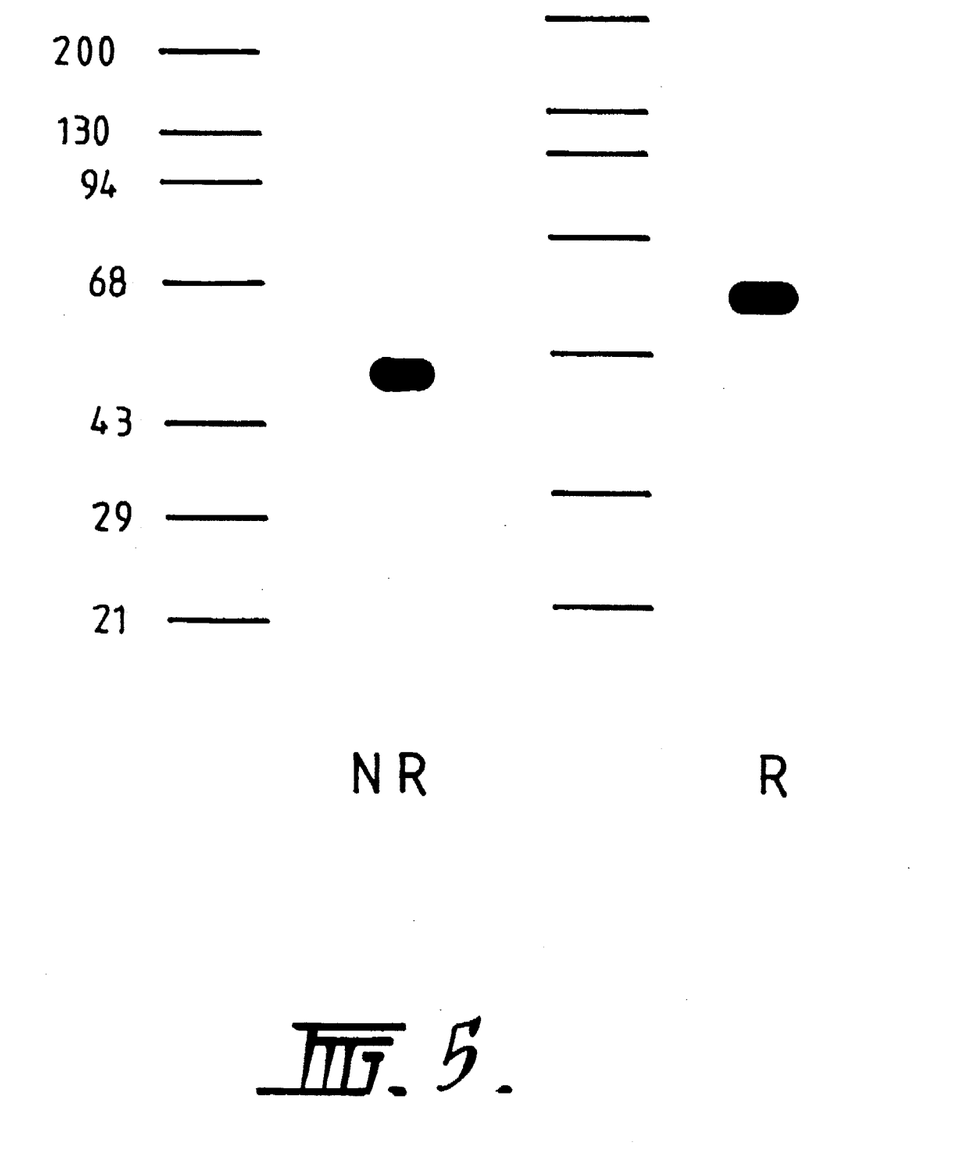
FIG. 5: SDS 5–20% exponential gradient polyacrylamide gel electrophoresis of purified mocarhagin under nonreducing (NR) and reducing (R) conditions stained with COO-MASSIE BLUE. Molecular weight standards are myosin (200 kDa), β-galactosidase (130 kDa), phosphorylase B (94 kDa), BSA (68 kDa), ovalbumin (43 kDa), carbonic anhydrase (29 kDa) and soybean trypsin inhibitor (21 kDa).
Figure 6:
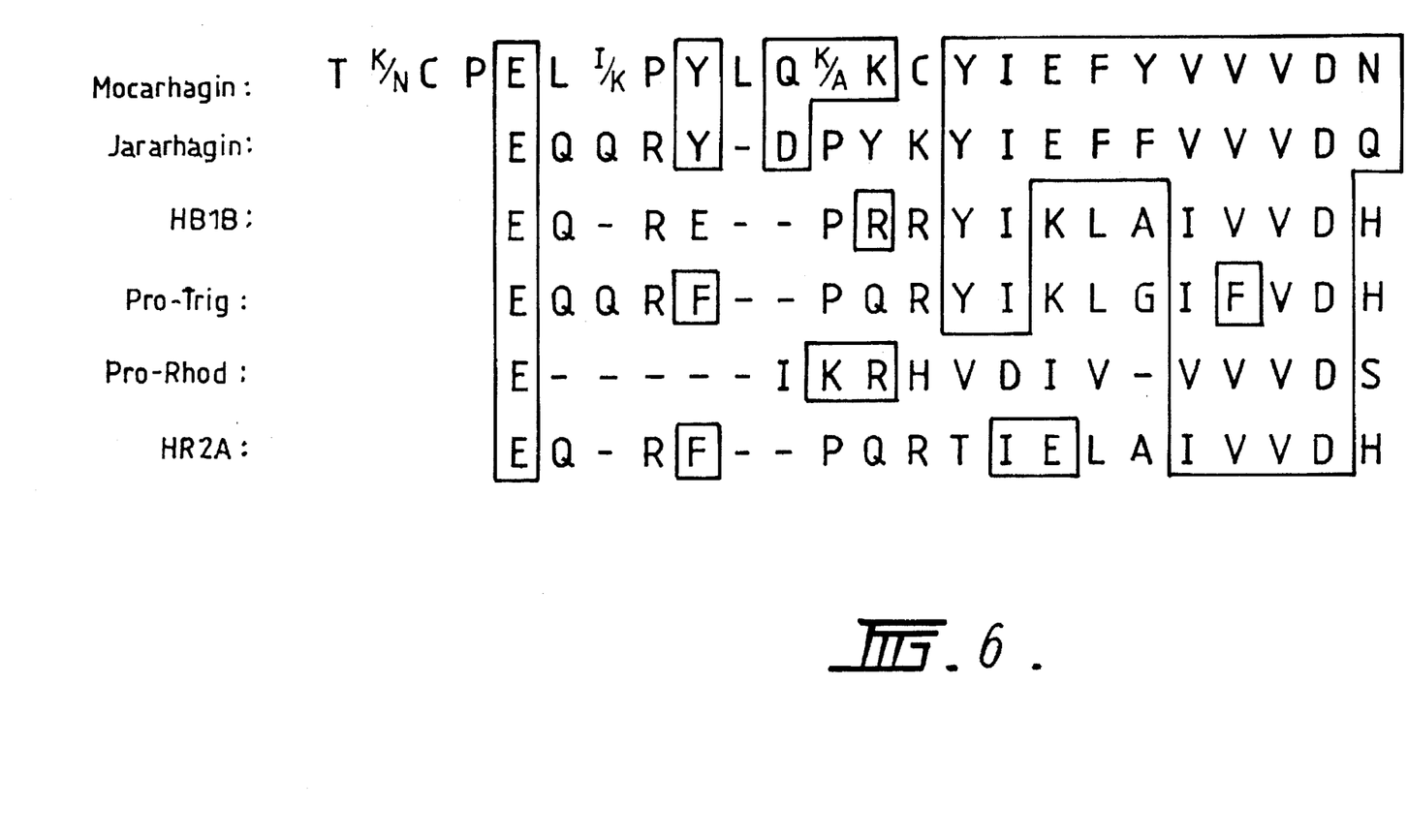

The major step in the preferred method of purification was heparin-affinity chromatography, based on the observation by Ogilvie & Gartner (1984) that cobra lectin-dependent hemagglutination was inhibitable by heparin. Mocarhagin was further purified by gel filtration on SEPHAROSE CL-6B, and had an apparent molecular weight by SDS-polyacrylamide gel electrophoresis of ~55 kDa under non-reducing and reducing conditions (FIG. 5). Typically, 1–2 mg of purified mocarhagin was obtained from 0.5 g of lyophilized venom. Mocarhagin stained weakly with periodic acid-Schiff reagent consistent with the presence of glycosylated residues. N-Terminal sequencing of purified mocarhagin was achieved up to 26 residues (FIG. 6), although the initial cycles showed multiple peaks that may be suggestive of a variable N-terminus.

The proteinase requires either calcium ion or zinc ion for activity and is substantially (actually fully) inhibited by excess EDTA and by high concentrations of DFP. Pretreatment of platelets with mocarhagin abolishes their ability to bind the adhesive ligand, von Willebrand Factor (vWF). This is due to proteolysis between Glu-282 and Asp-283 in the of-chain of the platelet vWF receptor, the GP Ib-V-IX complex, which occurs as the sole detectible cleavage on the intact platelet surface.

Figure 1:
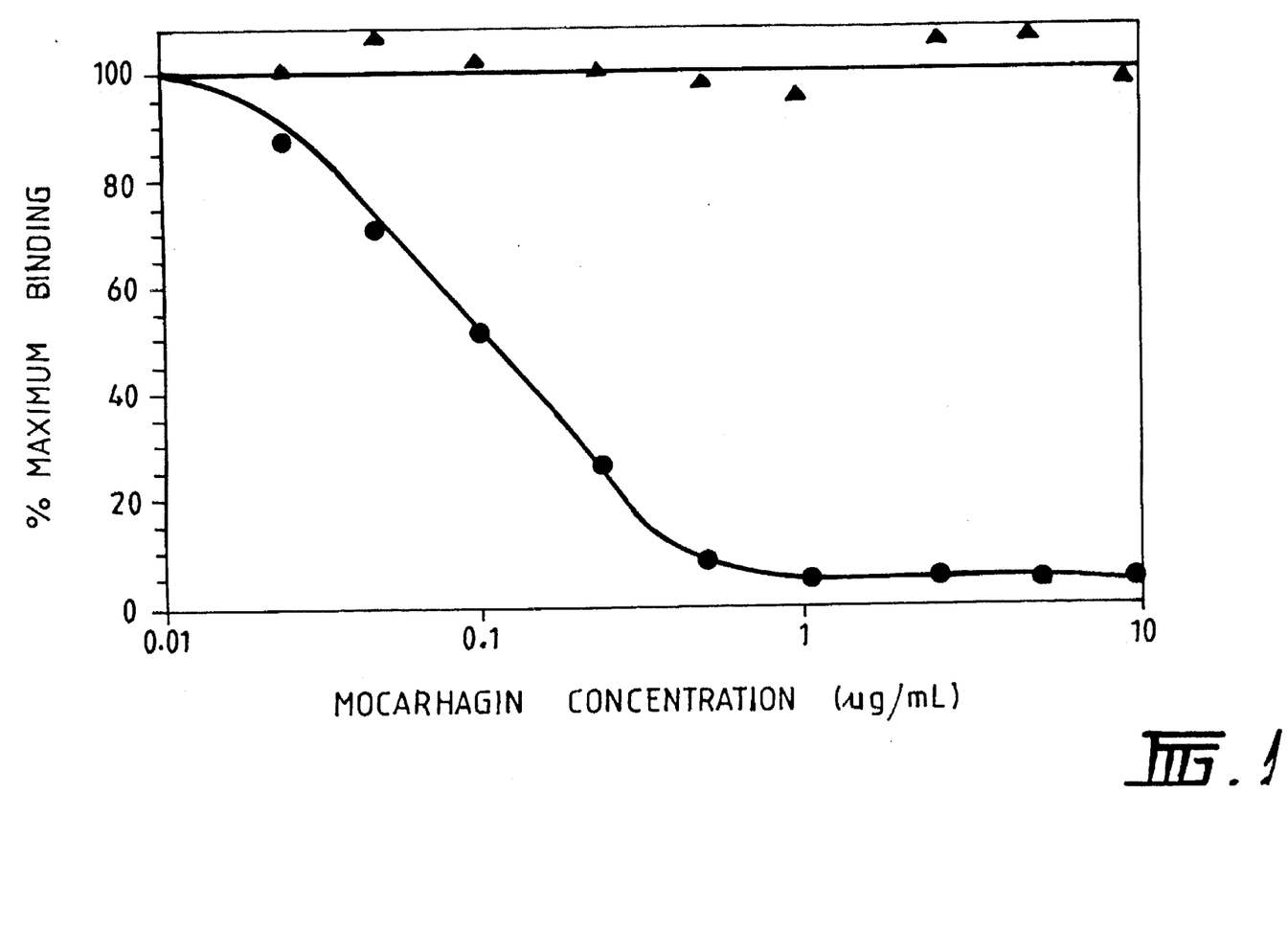
FIG. 1: Effect of mocarhagin on P-selectin binding to neutrophils. Neutrophils were pretreated for 30 min at room temperature with increasing concentrations of mocarhagin (circles), or with mocarhagin which had been treated with DFP (diisopropylfluorophosphate) (triangles).

In the course of studies with vWF, it was observed that mocarhagin was also a potent inhibitor of P-selectin binding to its myeloid receptor on neutrophils. Pretreatment of either neutrophils or HL60 cells with mocarhagin profoundly and reproducibly affected the subsequent binding of P-selectin to these treated cells with an apparent IC$_{50}$ (concentration of inhibitor giving 50% inhibition) of 0.1 µg/ml. A representative inhibition curve from multiple studies performed with both HL60 cells and neutrophils is shown in FIG. 1. Equivalent data were obtained regardless of whether the mocarhagin-treated cells were washed or not washed prior to the addition of P-selectin, i.e. whether the binding assay was actually performed in the absence or presence of the metalloproteinase. Further, inhibition was not reversed by incubation of the treated cells with fresh medium for up to three hours. Finally, mocarhagin had no effect on the molecular size of P-selectin or on its inherent ability to bind to myeloid cells (data not shown and see FIG. 2). Treatment of mocarhagin with DFP completely blocked its ability to inhibit P-selectin binding even if the myeloid cells were incubated with concentrations of DFP-treated mocarhagin up to 100 µg/ml (FIG. 1), a result in accord with proteolysis of the P-selectin receptor. Consistent with this view, the ability of mocarhagin to inhibit subsequent P-selectin binding was divalent-cation dependent, since incubation of neutrophils with excess EDTA prior to the addition of mocarhagin prevented its inhibitory effect. In addition, the time course of effect of mocarhagin was also consistent with a proteolytic event. If cells were incubated with 12 μg/ml of mocarhagin for ten seconds prior to the addition of EDTA and the cells then washed, P-selectin binding was reduced, even with this brief treatment, to 40% of normal. The concentrated supernatant from mocarhagin treated cells, after removal of mocarhagin by absorption with heparin-SEPHAROSE CL-6B, did not inhibit binding of P-selectin to HL60 cells indicating that a functional fragment of the P-selectin receptor was not released by mocarhagin treatment.

Although the data suggest that mocarhagin abolishes P-selectin binding to neutrophils by a proteolytic effect on the P-selectin receptor, cell surface labelling studies failed to identify a major substrate for mocarhagin on either neutrophils or HL60 cells. Both lactoperoxidase radioiodinated and periodate/tritium surface labelled neutrophils and HL60 cells were treated with mocarhagin and the resultant cells and supernatants compared with controls by one- and two-dimensional SDS-polyacrylamide gel analysis. With lactoperoxidase radioiodinated neutrophils and HL60 cells, no substrate or product was identified consistent with the exquisite substrate specificity of mocarhagin suggested by the platelet studies. With periodate-labelled cells, however, analysis under reducing conditions revealed the partial loss of a band of 40 kDa and several faint bands were evident in the supernatant. There were also increased amounts of a protein of 140 kDa in the supernatant of treated cells, although this glycoprotein band was also present in control supernatants and probably corresponds to the spontaneous shedding of small amounts of leukosialin. P-selectin has been previously established not to bind leukosialin. Since P-selectin ligand blotting assays have not identified a binding protein of 40 kDa molecular weight and since the 40-kDa glycoprotein was only partially cleaved at a concentration of mocarhagin much higher than that required to completely abrogate P-selectin binding (FIG. 1), it is probable that none of these minor events represents cleavage of the P-selectin receptor.

P-selectin glycoprotein-1 (PSGL-1) has recently been identified as a functional ligand for P-selectin on HL60 cells. A soluble form of PSGL-1, designated sPSGL-1.T7 (comprising amino acids 18-295 of PSGL-1), when expressed in COS cells with an 1,3/1,4 fucosyltransferase, also mediates P-selectin binding in a calcium-dependent manner (Sako et al.). One of the striking features of PSGL-1 is its similarity to the α-chain of platelet GP Ib. Both are sialomucins and each has immediately N-terminal to the mucin core a sequence rich in negatively-charged amino acids with three potential sulfated tyrosine residues (Sako et al.; Lopez et al. (1987) Proc. Natl. Acad. Sci. USA 78, 3403; Titani et al. (1987) Proc. Natl. Acad. Sci. USA 84, 5610). Since mocarhagin cleaves the α-chain of GP Ib within this negative charge/sulfated tyrosine cluster (FIG. 2), we speculated that mocarhagin may abrogate P-selectin binding to neutrophils and HL60 cells by cleaving near the N-terminus of PSGL-1, a result which would explain the failure to identify a major substrate for mocarhagin on myeloid cells.

Figure 3:
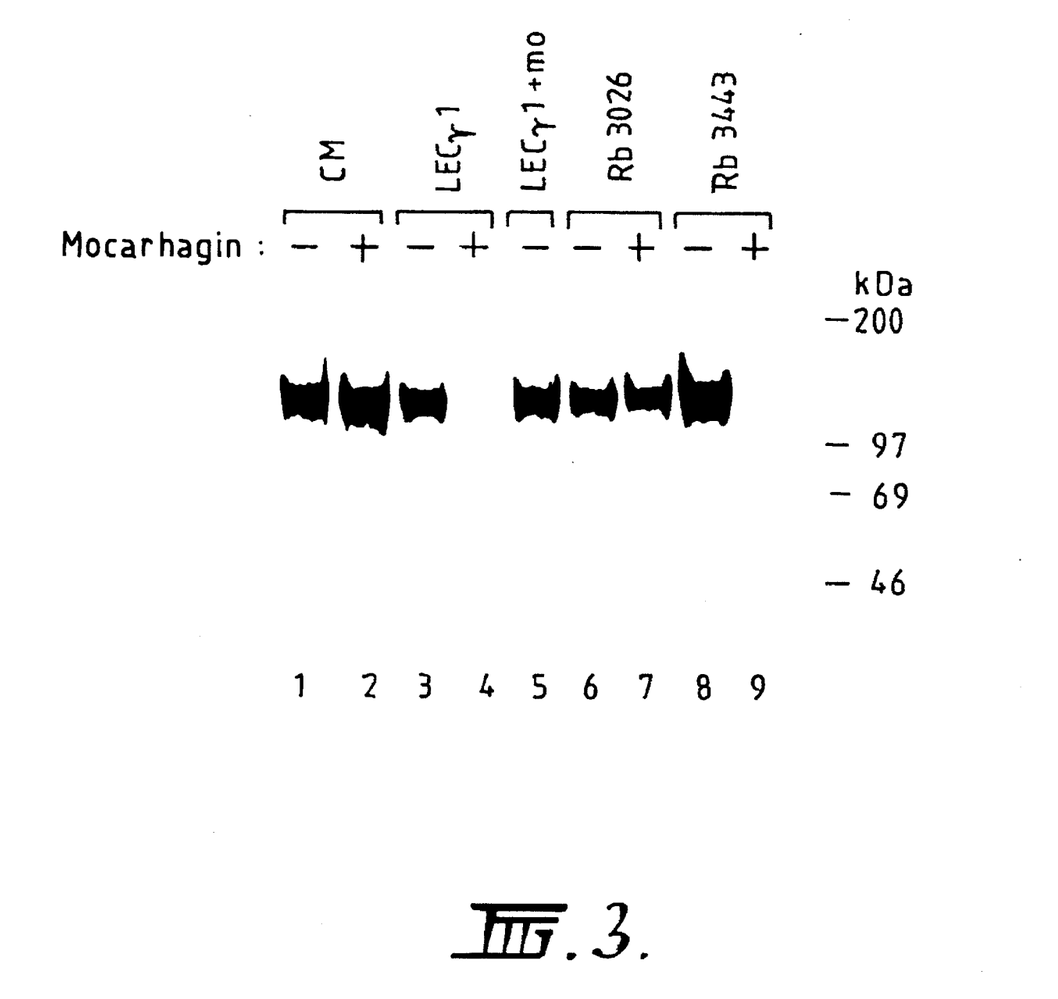
FIG. 3: Mocarhagin digestion of soluble P-selectin glycoprotein ligand. COS conditioned medium containing [$^{35}$S] methionine-labelled sPSGL-1.T7 was untreated (lanes 1,3, 5,6 and 8) or digested with 5 µg/ml mocarhagin (lanes 2,4,7 and 9). The samples were either directly electrophoresed (lanes 1 and 2), or precipitated with the P-selectin IgG chimera LECγ1 (lanes 3 and 4), or precipitated with LECγ1 which was pretreated with mocarhagin (LECγ1+mo; lane 5), or immunoprecipitated with Rb3026 (lanes 6 and 7) or with Rb3443 (lanes 8 and 9).

That this is indeed the case is confirmed by the data of FIG. 3. FIG. 3 shows that mocarhagin digestion of PACE cleaved, fucosylated sPSGL-1.T7 (comprising amino acids 42-295 of PSGL-1) results in only a minor shift, if any, in electrophoretic mobility of the protein on a SDS-polyacrylamide gel (lanes 1 and 2), but completely abolishes the binding of sPSGL-1.T7 to the P-selectin IgG chimera, LECγ1 (Sako et al.), coupled to Protein A SEPHAROSE (lanes 3 and 4). To exclude the possibility that the protease treatment interfered with LECγ1 binding by destroying the LECγ1 Protein A SEPHAROSE complex, the following control experiment was performed. LECγ1-Protein A SEPHAROSE beads were incubated with mocarhagin and then washed repeatedly to remove any residual protease. The protease treated beads were unaffected in their ability to bind sPSGL-1.T7 (lane 5). FIG. 3 also shows the reactivity of untreated and mocarhagin digested sPSGL-1 .T7 with two polyclonal antibodies. Rb3026 (Sako et al.), which was raised against COS produced sPSGL-1.T7, precipitates sPSGL-1 independent of mocarhagin digestion (lanes 6 and 7), whereas Rb3443, which was raised against the N-terminal peptide of PACE-cleaved PSGL-1 (QATEYEYLDYDFLPE, SEQ ID NO:2), only precipitates untreated sPSGL-1.T7 (lanes 8 and 9), indicating that the N-terminal epitope for Rb3443 is lost after mocarhagin digestion.

Figure 2:
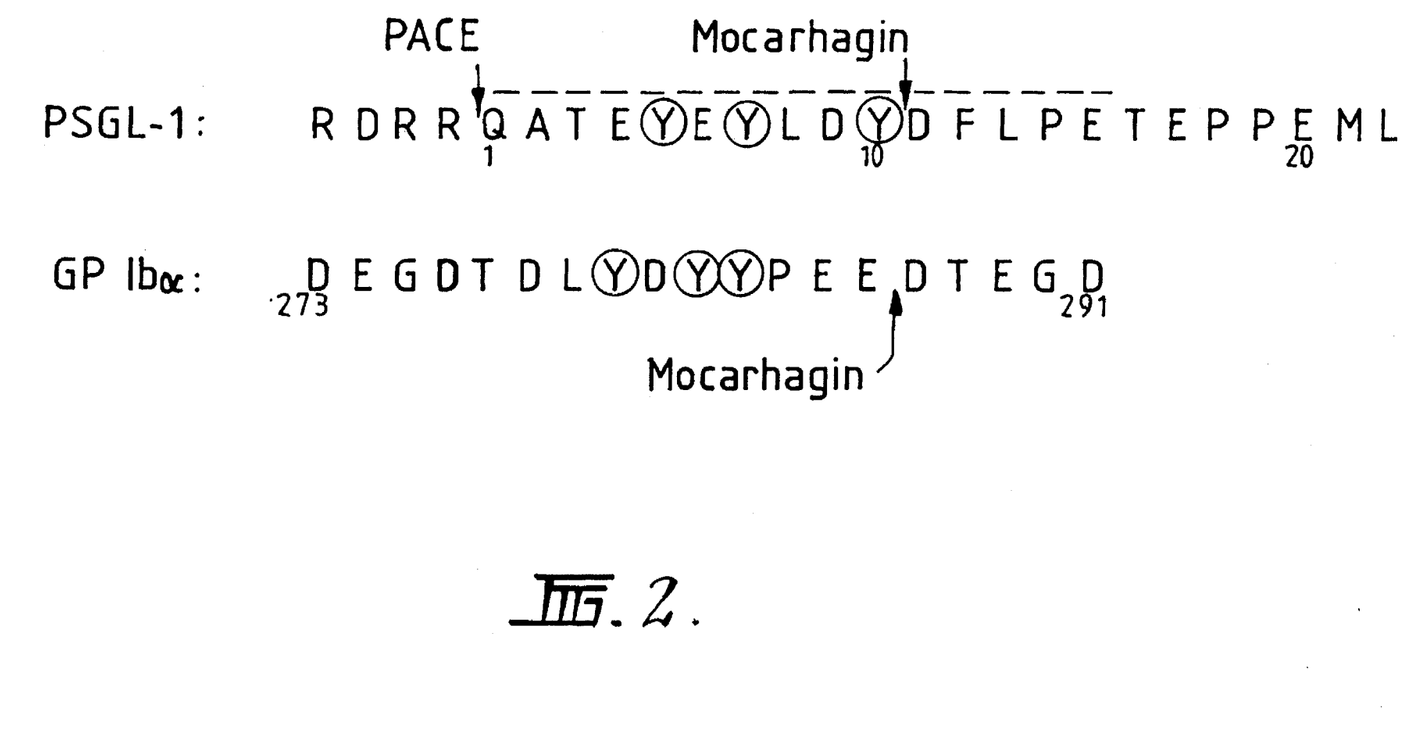
FIG. 2: Protease cleavage sites in PSGL-1. N-Terminal protein sequence of PSGL-1(SEQ. ID NO:7) indicating the cleavage sites for the signal peptidase, PACE and mocarhagin. The peptide that was used to raise the polyclonal antibody Rb3443 is overlined. The mocarhagin cleavage site for PSGL-1 is contrasted with the cleavage site on GP Ibα (SEQ. ID NO:8).

The exact mocarhagin cleavage site in PSGL-1 was determined by N-terminal microsequencing of purified, mocarhagin treated sPSGL-1.T7 protein (FIG. 2). The N-terminal sequence of mocarhagin-cleaved PSGL-1 was determined to be DFLPETEPPEML (SEQ ID NO:6). Mocarhagin removes the first ten amino acids from PACE cleaved sPSGL-1 .T7. This N-terminal peptide comprises three tyrosine residues, at least one of which is sulfated as determined by NMR. That the site of cleavage for mocarhagin was between Tyr-10 and Asp-11 was confirmed using the synthetic peptide, TEYEYLDYDFLPETE (SEQ ID NO:3), corresponding to residues 3-17 of mature PSGL-1. The mocarhagin cleavage sites on PSGL-1 and the α-chain of GP Ib are similar. Each occurs on the N-terminal site of an aspartate residue and to the C-terminal side of three potential sulfated tyrosine residues and within an overall negative charge cluster (FIG. 2). Since the proteolytic activity of mocarhagin is inhibited by heparin and polyanions (Ward et al., manuscript in preparation), this preference for negative charge cluster may in part explain the remarkable substrate specificity of mocarhagin.

Figure 4:
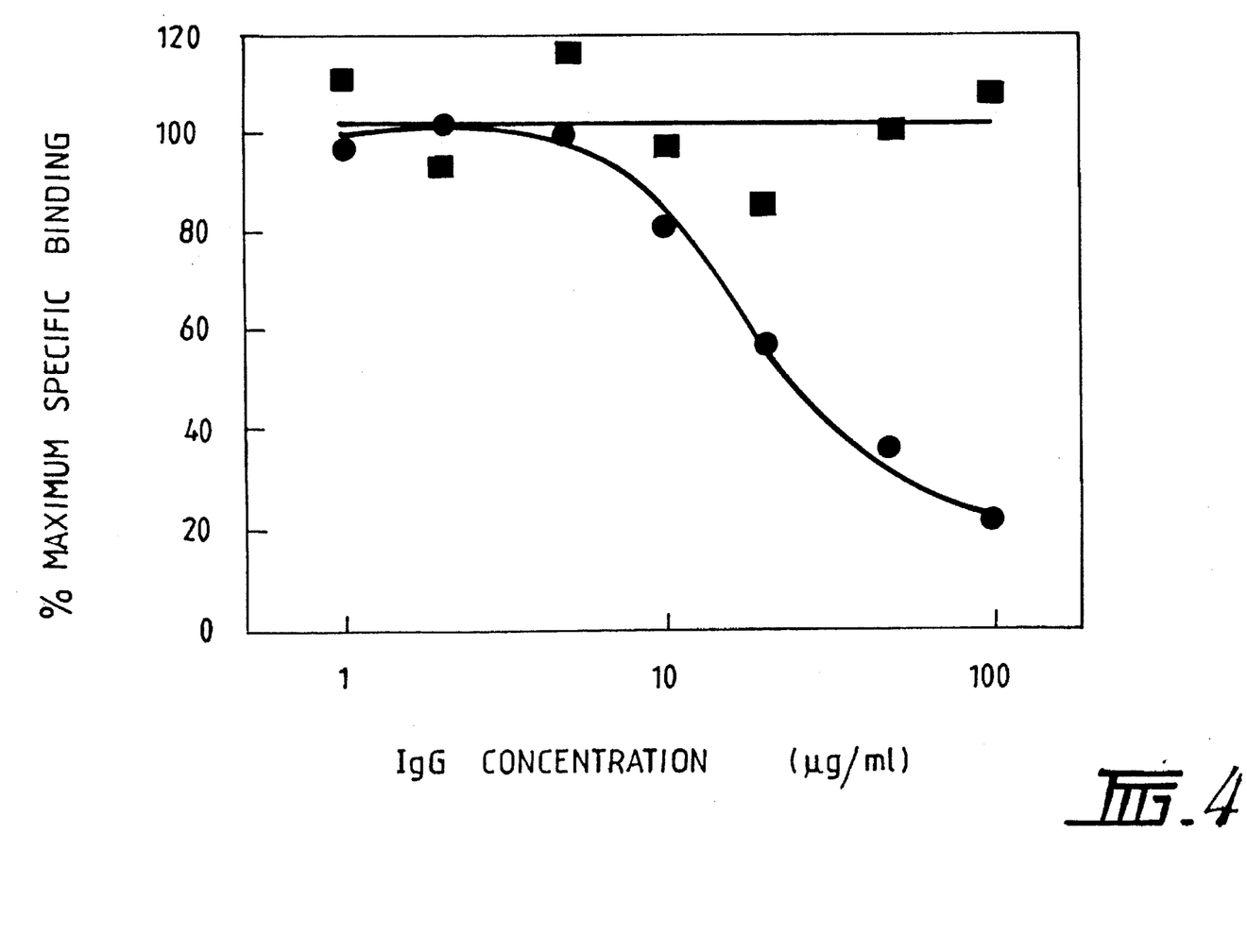
FIG. 4: Effect of anti-PSGL-1 IgG on P-selectin binding to neutrophils. Dose response curves for inhibition of specific binding of [$^{125}$I]P-selectin to neutrophils by polyclonal IgG against synthetic peptide sequences Gln-1 to Glu-15 (circles) and Asp-9 to Arg-23 (squares).

Confirmation of the critical importance of the N-terminal sequence of PSGL-1 in P-selectin binding was obtained using anti-peptide antibodies. P-selectin binding to neutrophils was inhibited by 80-90% by an affinity-purified polyclonal antibody against residues Gln- 1 to Glu- 15 of mature PSGL- 1 (QATEYEYLDYDFLPE, SEQ ID NO:2), but not by an affinity purified polyclonal antibody against residues Asp-9 to Arg-23 (DYDFLPETEPPEMLR, SEQ ID NO:4) (FIG. 4) or by nonimmune rabbit IgG (not shown). This result, together with the observed sensitivity of the myeloid P-selectin receptor for mocarhagin, is consistent with PSGL-1 being the predominant and major receptor for P-selectin on myeloid cells.

Although P-, E-, and L-selectin all recognize similar sialated carbohydrate structures such as sialyl-Lewis x, and many glycoproteins on the surface of myeloid cells contain sialyl-Lewis x, P-selectin appears to be highly specific in its recognition of PSGL-1 (Sako et al.). The present data suggest that one cause for this specificity is the negative charge/sulfated tyrosine cluster at the N-terminus of mature PSGL-1. Proteolytic removal of a N-terminal ten amino acid peptide by mocarhagin abolished P-selectin binding to PSGL-1 even though this sequence (QATEYEYLDY, SEQ ID NO:5) is not glycosylated. One explanation for this phenomenon is that removal of this sequence alters the conformational integrity of PSGL-1 such that P-selectin can no longer interact with critical carbohydrate structures associated with the PSGL-1 mucin core. This is unlikely for two reasons. Firstly, an affinity purified polyclonal antibody against the N-terminal fifteen amino acids of mature PSGL-1 also strongly inhibited P-selectin binding to neutrophils. Secondly, E-selectin like P-selectin also binds to PSGL-1, but, unlike P-selectin, E-selectin binds equally well to mocarhagin cleaved PSGL-1 suggesting that the carbohydrate recognition structures on PSGL-1 are still inherently accessible.

An alternate explanation of the present observations is that P-selectin binding to PSGL-1 is bimodal with P-selectin binding not only involving carbohydrate recognition but also the negative charge/sulfated tyrosine cluster. The approximately four order of magnitude difference in avidity for P-selectin binding to sialyl-Lewis x versus receptor is strongly suggestive that additional structural determinants are involved in binding of P-selectin to its myeloid receptor. This is further supported by the observation that P-selectin binding to myeloid cells is not only dependent on the N-terminal lectin domain, but also the adjacent EGF-like motif (Kansas et al. (1994) J. Cell Biol. 124,609).

For the purposes of the present invention, a protein is defined as having "mocarhagin proteolytic activity" when (1) it digests PSGL-1, such as in the PSGL-1 digestion assay described below, and/or (2) inhibits the binding of P-selectin to neutrophils or HL60 cells, such as in the binding inhibition assay described below. Preferably, in the PSGL-1 digestion assay complete cleavage of $^{35}$[S]-sPSGL-1.T7 is achieved in 20 min. using 10 µg/ml mocarhagin protein; more preferably in 20 min. using less than 1 µg/ml mocarhagin protein. Preferably, in the neutrophil/HL 60 binding inhibition assay the mocarhagin protein exhibits an $IC_{50}$ of less than about 100 µg/ml, more preferably less than about 1 µg/ml.

Fragments of mocarhagin having mocarhagin proteolytic activity are also encompassed by the present invention. Fragments of mocarhagin having mocarhagin proteolytic activity can be identified by the PSGL-1 digestion assay and neutrophil/HL60 binding inhibition assay described below. Fragments of mocarhagin may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. For the purposes of the present invention, all references to "mocarhagin protein" herein include mocarhagin and fragments having mocarhagin proteolytic activity.

Isolated mocarhagin protein may be useful in treating conditions characterized by P- or E-selectin mediated intercellular adhesion. Such conditions include, without limitation, myocardial infarction, bacterial or viral infection, metastatic conditions, inflammatory disorders such as arthritis, acute respiratory distress syndrome, asthma, emphysema, delayed type hypersensitivity reaction, systemic lupus erythematosus, thermal injury such as burns or frostbite, autoimmune thyroiditis, experimental allergic encephalomyelitis, multiple sclerosis, multiple organ injury syndrome secondary to trauma, diabetes, Reynaud's syndrome, neutrophilic dermatosis (Sweet's syndrome), inflammatory bowel disease, Grave's disease, glomerulonephritis, gingivitis, periodontitis, hemolytic uremic syndrome, ulcerative colitis, Crohn's disease, necrotizing enterocolitis, granulocyte transfusion associated syndrome, cytokine-induced toxicity, and the like. Mocarhagin protein may also be useful in organ transplantation, both to prepare organs for transplantation and to quell organ transplant rejection. Mocarhagin protein may be used to treat hemodialysis and leukophoresis patients. Mocarhagin protein may be used itself as an inhibitor of P- or E-selectin-mediated intercellular adhesion or to design inhibitors of P- or E-selectin-mediated intercellular adhesion. The present invention encompasses both pharmaceutical compositions containing mocarhagin protein and therapeutic methods of treatment or use which employ mocarhagin protein.

Mocarhagin protein may be used as a pharmaceutical composition when combined with a pharmaceutically acceptable carrier. Such a composition may contain, in addition to mocarhagin protein and carrier, diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, G-CSF, Meg-CSF, stem cell factor, and erythropoietin. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with mocarhagin protein, or to minimize side effects caused by the mocarhagin protein. Conversely, mocarhagin protein may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which mocarhagin protein is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., healing of chronic conditions characterized by P-selectin- or E-selectin-mediated cellular adhesion or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of mocarhagin protein is administered to a mammal having a P-selectin-mediated disease state. Mocarhagin protein may be administered in accordance with the method of the invention either alone or in combination with other therapies such as treatments employing cytokines, lymphokines or other hematopoietic factors. When co-administered with one or more cytokines, lymphokines or other hematopoietic factors, isolated mocarhagin protein may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated mocarhagin protein in combination with cytokine(s), lymphokine(s), other hematopoietic factor (s), thrombolytic or anti-thrombotic factors.

Administration of mocarhagin protein used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective mount of mocarhagin protein is administered orally, mocarhagin protein will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% mocarhagin protein, and preferably from about 25 to 90% mocarhagin protein. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of mocarhagin protein and preferably from about 1 to 50% mocarhagin protein.

When a therapeutically effective amount of mocarhagin protein is administered by intravenous, cutaneous or subcutaneous injection, mocarhagin protein will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to mocarhagin protein an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of mocarhagin protein in the pharmaceutical composition of the present invention will depend upon the nature and severity of the condition being treated, and on the nature of prior treatments which the patient has undergone. Ultimately, the attending physician will decide the amount of mocarhagin protein with which to treat each individual patient. Initially, the attending physician will administer low doses of mocarhagin protein and observe the patient's response. Larger doses of mocarhagin protein may be administered until the optimal therapeutic effect is obtained for the patient, and at that point the dosage is not increased further. It is contemplated that the various pharmaceutical compositions used to practice the method of the present invention should contain about 0.1 µg to about 100 mg of mocarhagin protein per kg body weight.

The duration of intravenous therapy using the pharmaceutical composition of the present invention will vary, depending on the severity of the disease being treated and the condition and potential idiosyncratic response of each individual patient. It is contemplated that the duration of each application of the mocarhagin protein will be in the range of 12 to 24 hours of continuous intravenous administration. Ultimately the attending physician will decide on the appropriate duration of intravenous therapy using the pharmaceutical composition of the present invention.

Mocarhagin protein of the invention may also be used to immunize animals to obtain polyclonal and monoclonal antibodies which specifically react with the mocarhagin protein and which may inhibit P-selectin-mediated cellular adhesion. Such antibodies may be obtained using the entire mocarhagin protein as an immunogen, or by using fragments of mocarhagin protein such as the soluble mature mocarhagin protein. Smaller fragments of the mocarhagin protein may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987).

EXAMPLES

The following examples are presented to illustrate, not to limit, the present invention.

Materials

*Naja mocambique mocambique* venom, diisopropyl fluorophosphate (DFP), aprotonin and pepstatin were purchased from Sigma, St. Louis, Mo.; Triton X-100 from BDH, Kilsyth, Victoria, Australia; RPMI tissue culture medium and Mono-Poly Resolving Medium (Ficoll-Hypaque) from Flow Laboratories, Irvine, Scotland; fetal bovine serum from Cytosystems, Castle Hill, N.S.W., Australia; heparin-Sepharose CL-6B, protein A SEPHAROSE and SEPHAROSE CL-6B from Pharmacia, Uppsala, Sweden; leupeptin from Auspep Pty. Ltd, Melbourne, Victoria, Australia. Sodium [$^{125}$I]iodide and sodium [$^3$H]borohydride from New England Nuclear, Wilmington, Del. The peptide, TEYEYLDYDFLPETE, corresponding to residues 3–17 of mature PSGL-1 was synthesized by Chiron Mimotopes Pty. Ltd., Melbourne, Australia.

Anti-peptide antibodies

Synthetic peptides based on the PSGL-1 amino acid sequences Gln-1 to Glu-15 and Asp-9 to Arg-23 containing an N-terminal cysteine residue to facilitate coupling were purified by reverse-phase HPLC and characterized by mass spectroscopy (Chiron). Peptides were coupled to keyhole limpet hemocyanin (Sigma) with m-maleimidobenzoyl-N-hydroxysuccinimide (Pierce, Rockford, Ill.) essentially as previously described (Lerner et al. (1981) Proc. Natl. Acad. Sci. USA 78, 3403) and rabbit antisera were raised by a standard protocol (Chong et al. (1994) Blood 83, 1535). Anti-peptide IgG was affinity purified on peptide coupled to a 1:1 mixture of Affi-gel 10 and 15 (0.5 mg peptide/5 ml resin and 0.5 mg peptide conjugated to BSA/5 ml resin) according to the manufacturer's instructions (Bio Rad, Richmond, Calif.). After washing with 0.01M Tris, 0.15M sodium chloride, pH 7.4 (TS buffer), bound IgG was eluted with 0.1M glycine, pH 2.8, peak fractions were immediately re-neutralized by addition of one-fifth volume of 1M Tris, pH 8, and the antibody was dialyzed into TS buffer. Non-immune rabbit IgG was prepared as previously described (Skinner et al. (1991) J. Biol. Chem. 266, 5371).

Purification of mocarhagin

The purification of mocarhagin from *Naja mocambique mocambique* venom was based on the heparin-binding properties of cobra lectins (Ogilvie & Gartner, 1984). Crude lyophilized venom (0.5 g) was solubilized in 10 mL water and loaded at 25 mL/h onto a 1.5×40-cm heparin-SEPHAROSE CL-6B column in TS buffer (0.01M Tris, 0.15M sodium chloride, pH 7.4) at 22 °C., and washed exhaustively with TS buffer. Bound protein was eluted with a linear 250-mL 0.15–1.0M sodium chloride gradient in 0.01M Tris, pH 7.4. Fractions containing mocarhagin as assessed by SDS-polyacrylamide gel electrophoresis were pooled and concentrated using an Amicon ultrafiltration device fitted with a YM30 membrane, and applied at 25 mL/h onto a 1.5×70-cm SEPHAROSE CL-6B column equilibrated in 0.01M Tris, 0.5M sodium chloride, pH 7.4. The peak mocarhagin fractions were pooled and dialyzed against TS buffer. DFP-treated mocarhagin was prepared by incubating 250 µg mocarhagin in 1 mL TS buffer with 8 mM (final concentration) DFP for 1 h at 22° C., followed by dialysis against TS buffer.

N-terminal Sequencing of Mocarhagin

Protein samples for N-terminal sequencing were dialyzed against 0.02% SDS and concentrated by vacuum centrifugation (Speedvac concentrator, Savant). N-terminal sequence was determined using an Applied Biosystems Model 470A protein sequencer equipped with an on-line Model 120A phenylthiohydantoin analyser. Polybrene was used as a carrier.

Binding of P-selectin to neutrophils and HL60 cells (Neutrophil/HL60 Binding Inhibition Assay)

Neutrophils were isolated from venous blood anticoagulated with heparin (20 units/ml, final concentration) according to the method of Bignold and Ferrante ((1987) J. Immunol. Meth. 96, 29). The neutrophils were >95% pure as evaluated by flow cytometry and >98% viable by trypan blue exclusion. HL60 cells were cultured in RPMI medium supplemented with 10% fetal calf serum. Immediately before use, cells were washed twice with phosphate-buffered saline (0.01M sodium phosphate, 0.15M sodium chloride, pH 7.4). Neutrophils and cultured cells were finally resuspended at $2\times10^7$/ml in RPMI medium supplemented with 1% fetal calf serum. Binding of $^{125}$I-labelled P-selectin (Skinner et al.) to neutrophils or HL60 cells was evaluated by incubating $^{125}$I-labelled P-selectin (0.5 µg/ml, final concentration) with cells ($1\times10^7$/ml, final concentration) at 22° C. in a final volume of 200 µl. After 30 min, duplicate 50 µl aliquots were withdrawn and loaded onto 200 µl of 17% (w/v) sucrose in RPMI medium containing 1% fetal calf serum. Neutrophils were pelleted at 8,750× g for 2 min. After careful aspiration of the supernatant, radiolabel associated with the cell pellets was measured in a -counter. Nonspecific binding of $^{125}$I-labelled P-selectin was assessed using a 50-fold excess of unlabelled P-selectin (Skinner et al.).

To examine the effect of pretreatment of neutrophils or HL60 cells with mocarhagin on P-selectin binding, washed cells ($2\times10^7$/ml) in RPMI made 1% in fetal calf serum were incubated in the presence or absence of 10 mM EDTA followed by mocarhagin (0.025–100 µg/ml, final concentrations) for 30 min at 22C. P-selectin binding was then either directly assessed or was assessed after centrifugation of the cells, which were then washed twice and finally resuspended in RPMI with 1% fetal calf serum. In some experiments, DFP-treated mocarhagin was employed in place of mocarhagin. To evaluate the effect of supernatant from mocarhagin treated cells on P-selectin binding, HL60 cells at $10^8$/ml in 0.01M TRIS, 0.015M sodium chloride, 0.001M calcium chloride, pH 7.4, were incubated with mocarhagin (12 µg/ml) for 10 min at 22° C. The supernatant collected following centrifugation at 1000× g for 10 min was made 0.1% in BSA and loaded onto a heparin SEPHAROSE CL-6B column (0.5×5 cm) to remove mocarhagin. The flow through was then tested for its effect on P-selectin binding to HL60 cells.

Effect of mocarhagin on surface-labelled neutrophils and HL60 cells

Washed neutrophils or HL60 cells were surface labelled by either lactoperoxidase-catalyzed radioiodination or with sodium periodate/sodium [$^3$H]borohydride (Berndt et al. (1981) J. Biol. Chem. 256, 59; Booth et al. (1984) J. Clin. Invest. 73, 291). Labelled cells in 0.01M Tris, 0.15M sodium chloride, 0.001M calcium chloride, pH 7.4, were incubated with mocarhagin (12 µg/ml, final concentration) or buffer for 10 min at 22° C. The cells were centrifuged at 150× g for 10 min, and washed twice with 0.01M Hepes, 0.15M sodium chloride, 0.001M EDTA, pH 7.4. The cells were then lysed with 1% (v/v) TRITON X-100 at 4° C. for 1 h in the presence of the following protease inhibitors: diisopropyl fluorophosphate (DFP) (0.5 mM), aprotonin (10 µg/ml), pepstatin (1M), leupeptin (100 µg/ml) and benzamidine (10 mM). The TRITON X-100 soluble fractions separated by centrifugation at 1,000× g for 10 min and the supernatants from the control and mocarhagin-treated cells were mixed with SDS sample buffer and then electrophoresed on a 5–15% SDS-polyacrylamide gel under reducing and non-reducing conditions, or on a two dimensional nonreduced/reduced gel as described by Phillips and Agin ((1977) J. Biol. Chem. 252, 2121). The gels were then stained with COOMASSIE BRILLIANT BLUE R and either prepared for fluorography according to Bonner and Lasky ((1974) Eur. J. Biochem. 46, 83) or for autoradiography.

Mocarhagin digestion of soluble PSGL-1 (PSGL-1 Digestion Assay)

COS cells were cotransfected with three plasmids encoding soluble PSGL-1 (pED.sPSGL-1.T7; Sako et al.), alpha 1,3/1,4 fucosyltransferase (pEA.3/4FT) and soluble PACE (pEA-PACE SOL; Wasley et al. (1993) J. Biol. Chem. 268, 8458–8465). [$^{35}$S]Methionine-labelled COS conditioned medium containing sPSGL-1.T7 was digested with 5 µg/ml mocarhagin in TBS, 2 mM calcium chloride; 1 mg/ml BSA for 20 min at 37C. The ability of sPSGL-1.T7 to bind P-selectin was assessed by precipitation with the P-selectin IgG chimera LECγ1 (Sako et al.) preabsorbed onto protein A SEPHAROSE beads in TBS, 2 mM calcium chloride, 1 mg/ml BSA for 4 h at 4C. A control experiment was also performed where the LECγ1 protein A SEPHAROSE beads were pre-treated with mocarhagin and then exhaustively washed prior to presentation of sPSGL-1.T7. For immunoprecipitation analysis of untreated and mocarhagin treated sPSGL-1.T7, the protease was inactivated by the addition of 5 mM EDTA. sPSGL-1.T7 was then immunoprecipitated with anti-PSGL-1 polyclonal antibodies Rb3026 (raised against COS produced sPSGL-1.T7; Sako et al.) or Rb3443 (raised against the N-terminal peptide of PACE cleaved PSGL-1: QATEYEYLDYDFLPE).

Purification o) sPSGL-1. T7

Conditioned medium from COS cells cotransfected with the three plasmids pED.sPSGL-1.T7, pEA. 3/4FT and pEA-PACE SOL, was diluted two fold with 50 mM MOPS, 150 mM NaCl, 0.5 mM $CaCl_2$ and 0.5 mM $MnCL_2$, pH 7.2, and applied to a column of lentil lectin-SEPHAROSE 4B equilibrated in the same buffer. After loading, the column was washed with the same buffer until the optical absorbance at 280 nm dropped to a stable baseline. The column was then eluted with the same buffer which had been adjusted to 0.5M α-methyl-mannoside and 0.3M NaCl.

Recombinant sPSGL-1.T7 was collected over 5-15 column volumes of this elution buffer. The lentil lectin eluate was then subjected to a 0-70% ammonium sulfate precipitation by adding 472 g ammonium sulfate per liter of column eluate at 4° C. After stirring for 30 min, the precipitate was suspended in a mimimal volume of TBS (20 mM Tris-HCl, 150 mM NaCl, pH 7.5) and applied to a TSK G4000SW$_{XL}$ gel filtration column equilibrated in TBS. The flow rate on the column was 0.5 ml/min and a guard column was employed. In aliquots of <250 μl, the resuspended ammonium sulfate pellet was injected on the column and fractions were analyzed by SDS-PAGE and Western analysis.

Identification of the cleavage site for mocarhagin on PSGL-1

20 μg purified sPSGL-1.T7 was digested with 1 μg mocarhagin in a total volume of 100 μl TBS containing 2 mM CaCl$_2$ for 1 h at 37° C. The protease was inactivated by addition of 10 mM EDTA. The sample was concentrated directly onto PRO-SPIN (Applied Biosystems, Foster City, Calif.) and subjected to N-terminal sequencing on an ABI m476 gas phase protein sequencer.

What is claimed is:

1. An isolated mocarhagin protein, wherein said mocarhagin protein is characterized by:
   (a) exhibiting an $IC_{50}$ of less than 100 µg/ml in a neutrophil/HL60 binding inhibition assay;
   (b) a molecular weight of approximately 55 kDa under reducing conditions;
   (c) a molecular weight of approximately 55 kDa under nonreducing conditions;
   (d) an N-terminal amino acid sequence comprising Thr-Xaa-Cys-Pro-Glu-Leu-Xaa-Pro-Tyr-Leu-Gln-Xaa-Lys-Cys-Tyr-Ile-Glu-Phe-Tyr-Val-Val-Val-Asp-Asn, wherein Xaa in the second position is Lys or Asn, the Xaa in the seventh position is Ile or Lys, and the Xaa in the twelfth position is Lys or Ala, (SEQ ID NO:1);
   (e) being capable of cleaving P-selectin glycoprotein ligand-1;
   (f) the ability to inhibit platelet binding to vWF;
   (g) having a requirement of calcium ion for activity;
   (h) having a requirement of zinc ion for activity;
   (i) having an activity inhibited by excess EDTA; and
   (j) having an activity inhibited by high concentrations of DFP.

2. A method of isolating mocarhagin protein of claim 1, said method comprising:
   (a) subjecting a composition comprising *Naja mocambique mocambique* snake venom to a heparin affinity chromatography column;
   (b) subjecting the eluate from said heparin affinity chromatography column to a gel filtration column; and
   (c) eluting said mocharhagin protein from said gel filtration column.

* * * * *

UNITED STATES PATENT AND TRADEMARK OFFICE
CERTIFICATE OF CORRECTION

PATENT NO.    : 5,659,018
DATED         : August 19, 1997
INVENTOR(S)   : Michael C. Berndt et al.

It is certified that error appears in the above-identified patent and that said Letters Patent is hereby corrected as shown below:

Title page,
Item [73], Assignee, "Genetics Institute, Inc., Cambridge, Mass" should read -- Baker Medical Research Institute, Victoria, Australia --.

Signed and Sealed this

Twelfth Day of August, 2003

JAMES E. ROGAN
*Director of the United States Patent and Trademark Office*